United States Patent
Fabbi et al.

(10) Patent No.: US 9,901,529 B2
(45) Date of Patent: Feb. 27, 2018

(54) HAIR COLOR COMPOSITION

(71) Applicant: Alfa Parf Group S.P.A., Bologna (IT)

(72) Inventors: Massimo Fabbi, Mozzo (IT); Alessandro Marcandalli, Osio Sotto (IT); Antonio Consoli, Urgnano (IT); Katiuscia Grevalcuore, Bergamo (IT); Emanuela Facchetti, Romano di Lombardia (IT)

(73) Assignee: ALFA PARF GROUP S.P.A., Bologna (IT)

( * ) Notice: Subject to any disclaimer, the term of this patent is extended or adjusted under 35 U.S.C. 154(b) by 0 days.

(21) Appl. No.: 15/291,097

(22) Filed: Oct. 12, 2016

(65) Prior Publication Data

US 2017/0105921 A1    Apr. 20, 2017

(30) Foreign Application Priority Data

Oct. 14, 2015  (EP) .................................. 15189810

(51) Int. Cl.
| | | |
|---|---|---|
| *A61Q 5/10* | (2006.01) | |
| *A61K 8/81* | (2006.01) | |
| *A61K 8/22* | (2006.01) | |
| *A61K 8/41* | (2006.01) | |
| *A61K 8/34* | (2006.01) | |
| *A61K 8/73* | (2006.01) | |

(52) U.S. Cl.
CPC ............. *A61K 8/8158* (2013.01); *A61K 8/22* (2013.01); *A61K 8/347* (2013.01); *A61K 8/41* (2013.01); *A61K 8/731* (2013.01); *A61K 8/8152* (2013.01); *A61Q 5/10* (2013.01); *A61K 2800/4324* (2013.01)

(58) Field of Classification Search
CPC ........ A61K 8/8158; A61K 8/22; A61K 8/347; A61K 8/8152; A61K 8/41; A61K 2800/4324; A61Q 5/10
See application file for complete search history.

(56) References Cited

U.S. PATENT DOCUMENTS

| | | | |
|---|---|---|---|
| 2006/0064823 A1* | 3/2006 | Marsh .................. | A61K 8/22 8/405 |
| 2013/0156716 A1* | 6/2013 | Yontz .................. | A61K 8/4973 424/70.6 |
| 2014/0090185 A1 | 4/2014 | Benn | |

FOREIGN PATENT DOCUMENTS

| | | |
|---|---|---|
| FR | 2994653 | 2/2014 |
| WO | 2013098335 A2 | 7/2013 |

OTHER PUBLICATIONS

European Search Report of Application EP 15189810 of May 2, 2016.

* cited by examiner

*Primary Examiner* — Eisa Elhilo
(74) *Attorney, Agent, or Firm* — Silvia Salvadori, P.C.; Silvia Salvadori

(57) ABSTRACT

The present invention relates to ready-to-use gel compositions for coloring hair in the form of an aqueous solution comprising:
- at least one Acrylates/Methacrylamide Copolymer;
- at least one cellulose derivative;
- at least one cross-linked polymer of acrylic acid or methacrylic acid or salts thereof;
- at least one oxidation dye and optionally at least one direct dye;
- at least one alkalizing agent;
hydrogen peroxide or an hydrogen peroxide adduct.

11 Claims, No Drawings

HAIR COLOR COMPOSITION

This application claims priority to and the benefit of European patent application 15189810.3 filed on Oct. 14, 2015, the content of which is incorporated herein by reference in its entirety.

The present invention relates to a ready-to-use gel composition for coloring human hair which is tacky to the hair, has a good manageability during application with bowl and brush, is drip-free during application on head, stable during storage time and provides color result on hair more even from growth to tips and bright.

BACKGROUND OF THE INVENTION

Throughout the years, there has been a desire to alter the color of synthetic and natural fibers. In particular, coloring of human hair has been sought in view of changing styles and fashion.

The coloring of hair is currently subject to the most varied trends. Whereas in the past hair was colored primarily to cover gray hair, today there is an increasing demand for integrating the hair color into current fashion as an expression of personality.

Now as before, two established methods of hair coloring are broadly applied. One is the semi-permanent system which consists of the possibility of coloring hair with colorants containing non-oxidative, direct dyes (often referred to as toners). Although the dyes used for this purpose are optimized for dyeing performance as well as for remaining on the hair as long as possible, the color shade gradually weakens with every hair washing Thus, depending on the type of hair and the used product, such colorants as a rule do not last more than a maximum of 10 hair washings. Although designed for direct dyeing, some of these dyes can also be applied in presence of hydrogen peroxide in order to intensify the color result and to obtain better root-to-tip evenness.

Besides the semi-permanent system, oxidation dyes have attained substantial cosmetic significance in the field of conventional hair dyeing. The color is created by reaction of certain primary intermediates and couplers in the presence of an oxidant. In addition to the creation of color effects, very high requirements are placed on oxidation dyes that are intended for the treatment of human hair. On the one hand, the dyes must be safe from a toxicological and dermatological point of view. Moreover, it must be possible, by a combination of suitable primary intermediates and couplers, to produce a wide range of different color nuances. Furthermore, the hair colorations produced are required to have good wash fastness, light fastness, perspiration resistance, resistance to permanent wave treatments, acid resistance, base resistance and abrasion resistance. At any rate, such hair colorations must remain stable for at least four to six weeks under normal everyday conditions.

The oxidative system is based on the reaction of so called primary intermediates with couplers; both molecule types are practically colorless. In presence of air or oxidants such as hydrogen peroxide, primary aromatic amines with an additional hydroxy, amino, mono- or di-substituted amino groups in the para or ortho position react with couplers of the resorcinol, m-aminophenol, m-phenylenediamine or 1-naphthol type. Some years ago, a new primary intermediate, a substituted 4,5-diaminopyrazole, was introduced to provide intense red shades with most of the commonly used couplers.

As the size of the dye molecules formed in the hair is larger than the size of the highly diffusible starting primary intermediates and couplers, no significant fading normally occurs after dyeing. Therefore the oxidative hair coloring which produces a very durable coloring result is also called "permanent" system.

The base used for pH adjustment has preferably been ammonium hydroxide. The advantage of using ammonium hydroxide is that the combination with hydrogen peroxide provides slight enlightening of the hair. During processing, enlightening occurs in parallel with coloring the hair. In this connection, the lightening effect is essential for providing even color results.

A number of primary hydroxyalkylamines which are mostly odorless can be used instead of ammonium hydroxide, which has a characteristic pungent odor. As alkanolamines are not volatile under hair coloring conditions the hair has to be well rinsed after processing.

Over the years, classes for hair colorants have been established. Hair colorants based on cream or gel are very common in European countries. Liquid formulations which, when mixed with aqueous hydrogen peroxide compositions, form a gel are preferred in numerous American countries. The colorants can either be prepared and applied by the traditional way; in particular hairdressers prepare the ready-to-use mixtures in a bowl and apply it by a brush; or compositions are shakable and are therefore preferentially mixed with the developer composition in a vessel. Then the colorants are applied from the vessel via a nozzle or a system of nozzles which have the design of a comb. The latter is especially suitable for applications at home. In all these cases it is ensured that the hair colorants remain exactly where applied and do not drip from the head during time application.

The gel base for oxidation dyes should be the choice when the hairdresser wants a transparent texture that is easy to mix with hydrogen peroxide, changing itself into a cream appearance upon mixing or, in some cases, with transparent peroxide, maintains the transparence of mixture. A first example of gel in oxidation tint was disclosed in FR1311807.

Despite considerable advantages in terms of aesthetic appearance and easiness to mix, the gel can also have significant inconveniences.

Depending on the individual condition of the hair which can be from non-damaged to damaged, from dry to greasy, from thin to thick, from short to long, the composition on-head may not always have the required stability over the whole processing time. Especially at extended processing times, compositions have a tendency to run down from the head so an important amount of composition cannot be retained by the hair with reduced efficacy of the treatment.

There is still a need for agents that can impart uniform coloration with high intensity and vividness as well as a good gray coverage capability is a continuous focus of development. Finally current hair dyes, due to the plurality of ingredients, have shown to frequently possess unsatisfactory rheological properties. These are particularly evident from the viscosity variation during shelf life. For example, agents that thicken during storage are associated with issues such as lose of viscosity stability, dosing and application. Another need is to increase tackiness to the hair fiber and manageability during application with bowl and brush.

Consequently, an object of the invention is to mitigate the above mentioned disadvantages of oxidative gel hair dyes by improving rheological properties, viscosity stability and manageability during application with bowl and brush, tackiness to the hair, brightness and evenness from growth to the tips.

DESCRIPTION OF THE INVENTION

Surprisingly, it has been found that this object can be reached by applying a ready-to-use gel composition for coloring hair in the form of an aqueous solution comprising:
- at least one Acrylates/Methacrylamide Copolymer;
  - at least one cellulose derivative;
    - at least one cross-linked polymer of acrylic acid or methacrylic acid or salts thereof;
  - one or more oxidation dyes and optionally one or more direct dyes;
  - at least one alkalizing agent;
  - hydrogen peroxide or alternatively a hydrogen peroxide adduct.

The composition may optionally comprise auxiliary agents and/or additives, as needed.

The composition may be used for simultaneous lightening and coloring hair, especially human hair.

Acrylates/Methacrylamide Copolymers are for instance described in U.S. Pat. No. 8,821,843. When the Acrylates/Methacrylamide Copolymer is added to the composition, the obtained formula is clear and not opaque (it is transparent), when mixed and applied on-head it does not drip down during processing time, the manageability during application with bowl and brush is easier because it does not drip from the brush, the tackiness to the hair is increased, brightness and evenness from growth to tips is improved and the composition hasn't significant rheological properties fluctuation.

Especially useful Acrylates/Methacrylamide Copolymer may be obtained from BASF with the trade name LUVISET® ONE.

Acrylates/Methacrylamide Copolymer may be used in an amount from 0.01 to 10 percent by weight of the composition, preferably from 0.05 to 4% by weight, more preferably from 0.1 to 2.5% by weight.

Suitable cellulose derivatives include acetyl, methyl or ethyl celluloses, hydroxyalkyl celluloses or carboxyalkyl celluloses. Hydroxyethylcellulose is particularly preferred. It may be supplied by ASHLAND Inc. with the trade name of NATROSOL® 250HR/HHR or from SHINETSU with the trade name TYLOSE®. This polymeric thickener is included in an amount of 0.01 to 4.0 wt %, particularly 0.05 to 3 wt %, each relative to the total weight of the composition.

Suitable homopolymers of acrylic acid are optionally crosslinked polyacrylic acids (such as a carbomer which is available under the trade name CARBOPOL® manufactured by Lubrizol or SYNTHALEN® manufactured by 3V Sigma) as well as polyacrylates as their partially or almost completely deprotonated salt forms. Here, the acidic groups may be fully or partially present as sodium, potassium, ammonium, mono- or tri-ethanolammonium salts. Allyl ethers of pentaerythritol, of sucrose and of propylene glycol as well as ethylene glycol dimethacrylate are preferred crosslinking agents. Examples of homopolymers of methacrylic acid are polymethacrylic acids and polymethacrylates optionally crosslinked.

The cross-linked polymer of acrylic or methacrylic acid or salts thereof are preferably included in the gel of the invention in an amount of 0.1 to 5.0% by weight, preferably 0.3 to 3.0%, more preferably 0.5 to 2.5% relative to the total weight of the agent.

As dye forming components, common primary intermediates and couplers as well as known dye intermediates can be used.

The primary intermediates may be derivatives of p-phenylenediamine, p-amino-phenol or 4,5-diaminopyrazole.

Examples of suitable precursors which may function as primary intermediates are: 1,4-diamino-benzene (p-phenylenediamine); 1,4-diamino-2-methyl-benzene (p-toluylenediamine); 1,4-diamino-2,6-dimethyl-benzene; 1,4-diamino-3,5-diethyl-benzene; 1,4-diamino-2,5-dimethyl-benzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl)benzene; 2,5-diaminobiphenyl; 1,4-diamino-2-methoxymethyl-benzene; 1,4-diamino-2-aminomethylbenzene; 1,4-diamino-2-hydroxymethyl-benzene; 1,4-diamino-2-(2-hydroxyethoxy)benzene; 2-(2-(acetylamino)ethoxy)-1,4-diaminobenzene; 4-phenylamino-aniline; 4-dimethylamino-aniline; 4-diethylamino-aniline; 4-dipropylamino-aniline; 4-[ethyl(2-hydroxyethyl)amino]-aniline; 4-[di(2-hydroxyethyl)amino]-aniline; 4-[di(2-hydroxyethyl)amino]-2-methyl-aniline; 4-[(2-methoxyethyl)amino]-aniline; 4-[(3-hydroxypropyl)amino]-aniline; 4-[(2,3-dihydroxypropyl)amino-aniline; 1,4-diamino-2-(2-hydroxyethyl)-benzene; 1,4-diamino-2-(1-methylethyl)-benzene; 1,3-bis[(4-aminophenyl)(2-hydroxyethyl)amino]-2-propanol; 1,4-bis[(4-aminophenyl)amino]-butane; 1,8-bis(2,5-diaminophenoxy)-3,6-dioxaoctane; 4-amino-phenol; 4-amino-3-methyl-phenol; 4-amino-3-(hydroxymethyl)-phenol; 4-amino-3-fluoro-phenol; 4-methylamino-phenol; 4-amino-2-(aminomethyl)-phenol; 4-amino-2-(hydroxymethyl)-phenol; 4-amino-2-fluorophenol; 4-amino-2-[(2-hydroxyethyl)-amino]methylphenol; 4-amino-2-methyl-phenol; 4-amino-2-(methoxymethyl)-phenol; 4-amino-2-(2-hydroxyethyl)-phenol; 5-amino-salicylic acid; 2,5-diamino-pyridine; 2,4,5,6-tetramine-pyrimidine; 4,5-diamino-1-(2-hydroxyethyl)-1H-pyrazole; 4,5-diamino-1-(1-methylethyl)-1H-pyrazole; 4,5-diamino-1-[(4-methylphenyl)methyl]-1H-pyrazole; 1-[(4-chlorophenyl)methyl]-4,5-diamino-1H-pyrazole; 4,5-diamino-1-methyl-1H-pyrazole; 2-aminophenol; 2-amino-6-methylphenol; (p-Ammoniophenyl)bis(2-hydroxyethyl)ammonium; 2-[(3-aminopyrazolo[1,5-a]pyridin-2-yl)oxy]ethanol hydrochloride (Hydroxyethoxy aminopyrazolopyridine HCl) and 2-amino-5-methylphenol.

The couplers may be of the m-dihydroxybenzene type, m-aminophenol type, m-phenylenediamine type or of the o-aminophenol type.

Examples of couplers suitable for the invention include 2,6-diamino-pyridine; 2-amino-4-[(2-hydroxyethyl)amino]anisole; 2,4-diamino-1-fluoro-5-methylbenzene; 2,4-diamino-1-methoxy-5-methylbenzene 2,4-diamino-1-ethoxy-5-methyl-benzene; 2,4-diamino-1-(2-hydroxyethoxy)-5-methylbenzene; 2,4-di[(2-hydroxyethyl)amino]-1,5-dimethoxybenzene; 2,3-diamino-6-methoxy-pyridine; 3-amino-6-methoxy-2-(m ethylamino)pyridine; 2,6-diamino-3,5-dimethoxypyridine; 3,5-diamino-2,6-dimethoxy-pyridine; 1,3-diaminobenzene; 2,4-diamino-1-(2-hydroxyethoxy)benzene; 1,3-diamino-4-(2,3-hydroxypropoxy)benzene; 2,4-diamino-1,5-di(2-hydroxyethoxy)-benzene; 1-(2-aminoethoxy)-2,4-diaminobenzene; 2-amino-1-(2-hydroxyethoxy)-4-methylaminobenzene; 2,4-diaminophenoxyacetic acid ester; 3-[di(2-hydroxyethyl)amino]aniline; 4-amino-2-di[(2-hydroxyethyl)amino]-1-ethoxy-benzene; 5-methyl-2-(1-methylethyl)phenol; N-(3-dimethylaminophenyl)-urea; 3-[(2-hydroxyethyl)amino]aniline; 3-[(2-aminoethyl)amino]aniline; 1,3-di(2,4-diaminophenoxy)propane; di(2,4-diaminophenoxy)methane; 1,3-diamino-2,4-dimethoxybenzene; 2,6-bis(2-hydroxyethyl)aminotoluene; 4-hydroxyindole; 3-dimethylaminophenol; 3-diethylaminophenol; 5-amino-2-methylphenol; 3-amino-2,6-dimethylphenol; 5-amino-4-fluoro-2-methyl-phenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methyl-phenol; 3-amino-2-chloro-6-methylphenol; 3-aminophenol; 2-[(3-hydroxyphenyl)-amino]acetamide; 5-[(2-hydroxyethyl)amino]-4-methoxy-2-methylphenol; 5-[(2-hydroxyethyl)amino]-2-methylphenol; 3-[(2-hydroxyethyl)amino]-phenol; 3-[(2-methoxyethyl)amino]-phenol; 5-amino-2-ethyl-phenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-m ethylphenol; 2-amino-3-hydroxypyridine; 5-amino-4-chloro-2-methylphenol; 1-naphthol; 2-methyl-1-naphthol; 1,5-dihydroxynaphthalene; 1,7-dihydroxy-naphthalene; 2,3-dihydroxynaphthalene, 2,7-dihydroxy-naphthalene; 2-methyl-1-naphthol-acetate; 1,3-dihydroxybenzene; 1-chloro-2,4-dihydroxy-benzene; 2-chloro-1,3-dihydroxybenzene; 1,2-dichloro-2,4-dihydroxy-4-methylbenzene; 1,5-dichloro-2,4-dihydroxy-benzene; 1,3-dihydroxy-2-methyl-benzene; 3,4-methylene dioxy-phenol; 3,4-methylene dioxy-aniline; 6-bromo-1-hydroxy-3,4-methylenedioxybenzene; 3,4-diaminobenzoic acid; 3,4-dihydroxy-6-hydroxy-1,4(2H)benzoxazine; 6-amino-3,4-dihydro-1,4(2H)-benzoxazine; 3-methyl-1-phenyl-5-pyrazolone; 5,6-dihydroxyindole; 5,6-dihydroxyindoline; 5-hydroxyindole; and 6-hydroxyindole.

The primary intermediates and couplers can be used both as free bases and also in form of their physiologically compatible salts with inorganic or organic acids, such as hydrochloric acid, sulfuric acid, phosphoric acid, lactic acid or citric acid.

The composition according to the invention can also contain a further dye intermediate, such as 6-amino-2-methylphenol and 2-amino-5-ethylphenol.

Even though a broad shade palette can be achieved by combinations of primary intermediates and couplers, it might be necessary to add direct dyes to the oxidative colorants in order to obtain brilliant reflexes on the dyed hair or to achieve a fashion colored gel. Some of these dyes are also called "booster dyes". The direct dyes that may be used according to the invention are preferably chosen from neutral, acidic or cationic nitrobenzene direct dyes; neutral, acidic or cationic azo direct dyes; neutral, acidic or cationic quinones and in particular anthraquinone direct dyes, azine direct dyes, triarylmethane direct dyes, indoamine direct dyes and natural direct dyes.

Said direct-dyeing compounds can be for instance:
aromatic nitro dye compounds (neutral dyes), such as 2-amino-3-nitrophenol; 2-[(2-hydroxyethypamino]-1-methoxy-5-nitrobenzene; 1-(2-hydroxyethoxy)-3-methylamino-4-nitrobenzene; 2,3-(dihydroxyprop oxy)-3-methylamino-4-nitrobenzene; 1-[(2-ureido-ethyl)amino]-4-nitrobenzene; 4-[(2-hydroxyethyl)amino]-3-nitro-1-methylbenzene; 1-[(2-hydroxyethyl)amino]-2-nitrobenzene (HC Yellow No. 2); 1-(2-hydroxyethoxy)-2-[(2-hydroxyethyl)amino]-5-nitrobenzene (HC Yellow No. 4); 1-amino-2-[(2-hydroxyethyl)amino]-5-nitrobenzene (HC Yellow No. 5); 4-[(2,3-dihydroxypropyl)amino]-3-nitro-1-trifluoromethylbenzene (HC Yellow No. 6); 3-[(2-amino-ethyl)amino]-1-methoxy-4-nitrobenzene hydrochloride (HC Yellow No. 9); 1-chloro-2,4-bis-[(2-hydroxyethyl)amino]-5-nitrobenzene (HC Yellow No. 10); 2-[(2-hydroxyethyl)amino]-5-nitrophenol (HC Yellow No. 11); 1-chloro-4-[(2-hydroxyethyl)amino]-3-nitrobenzene (HC Yellow No. 12); 4-[(2-hydroxyethyl)amino]-3-nitro-1-trifluoromethyl-benzene (HC Yellow No. 13); 4-[(2-hydroxyethyl)amino]-3-nitro-benzonitrile (HC Yellow No. 14); 4-[(2-hydroxyethyl)amino]-3-nitrobenzamide (HC Yellow No. 15); 1,4-diamino-2-nitrobenzene; 1,4-bis[(2-hydroxyethyl)amino]-2-nitrobenzene; 2-amino-4,6-dinitro-phenol; 4-amino-3-nitrophenol; 1-amino-5-chloro-4-[(2-hydroxyethyl)amino]-2-nitrobenzene; 4-[(2-hydroxyethyl)amino]-3-nitrophenol; 1-[(2-aminoethyl)amino]-4-(2-hydroxyethoxy)-2-nitrobenzene (HC Orange No. 2); 4-(2,3-dihydroxyprop oxy)-1-[(2-hydroxyethyl)amino]-2-nitrobenzene (HC Orange No. 3); 2-[(2-hydroxyethyl)amino]-4,6-dinitro-phenol; 4-ethylamino-3-nitrobenzoic acid; 2-[(4-amino-2-nitrophenyl)amino]-benzoic acid; 2-chloro-6-ethylamino-4-nitrophenol; 2-amino-6-chloro-4-nitrophenol; 4-[(3-hydroxypropyl)amino]-3-nitrophenol; 2,5-diamino-6-nitropyridine; 1,2,3,4-tetrahydro-6-nitroquinoxaline; 4-amino-2-nitro-diphenylamine (HC Red No. 1); 4-amino-1-[(2-hydroxyethyl)amino]-2-nitrobenzene (HC Red No. 3); 1-amino-4-[(2-hydroxyethyl)amino]-2-nitrobenzene (HC Red No. 7); 1-amino-5-chloro-4-[(2,3-dihydroxypropyl)amino]-2-nitrobenzene (HC Red No. 10); 5-chloro-1,4-[di(2,3-dihydroxypropyl)amino]-2-nitrobenzene (HC Red No. 11); 1-amino-4-[di(2-hydroxyethyl)amino]-2-nitrobenzene hydrochloride (HC Red No. 13); 7-amino-3,4-dihydro-6-nitro-2H-1,4-benzoxazine (HC Red No. 14); 4-[(3-hydroxypropyl)amino]-3-nitrophenol (HC Red BN); 1-amino-3-methyl-4-[(2-hydroxyethyl)amino]-6-nitrobenzene (HC Violet No. 1); 1-(3-hydroxypropylamino)-4-[di(2-hydroxyethyl)amino]-2-nitrobenzene (HC Violet No. 2); 1-(2-hydroxyethyl)amino-2-nitro-4-[di(2-hydroxyethyl)amino]-benzene (HC Blue No. 2); 1-methylamino-4-[methyl-(2,3-dihydroxypropyl)amino]-2-nitrobenzene (HC Blue No. 6); 1-[(2,3-dihydroxypropyl)amino]-4-[ethyl-(2-hydroxyethyl)amino]-2-nitrobenzene hydrochloride (HC Blue No. 9); 1-[(2,3-dihydroxypropyl)amino]-4-[methyl-(2-hydroxyethyl)amino]-2-nitrobenzene (HC Blue No. 10); 4-[di(2-hydroxyethyl)amino]-1-[(2-methoxyethyl)amino]-2-nitrobenzene (HC Blue No. 11); 4-[ethyl-(2-hydroxyethyl)amino]-1-[(2-hydroxyethyl)amino]-2-nitrobenzene hydrochloride (HC Blue No. 12); 2-((4-amino-2-nitrophenyl)amino)-5-dimethylaminobenzoic acid (HC Blue No. 13); 2,2'-[(2-Nitro-1,4-phenylene)diimino]bisethanol (N,N'-BIS(2-HYDROXYETHYL)-2-NITRO-P-PHENYLENEDIAMINE), 2-amino-6-chloro-4-nitrophenol.

basic dyes (cationic dyes), such as 2-[2-((2,4-dimethoxyphenyl)amino)ethenyl]-1,3,3-trimethyl-3H-indolium-chloride (C.I. 48055; Basic Yellow 11); 2-[7-(Diethylamino)-2-Oxo-2H-1-benzopyran-3-yl]-1,3-dimethyl-1H-Benzimidazolium Chloride (Basic Yellow 40); 3-methyl-1-phenyl-4-[(3-(trim ethylammonio)phenyl)azo]-pyrazol-5-one-chloride (C.I. 12719; Basic Yellow 57); 1-methyl-4-((methylphenylhydrazono)methyl)-pyridinium methylsulfate (Basic Yellow 87); 2-[(4-aminophenyl)azo]-1,3-dimethyl-1H-imidazolium chloride (Basic Orange 31); 3,7-diamino-2,8-dimethyl-5-phenylphenazinium-chloride (C.I. 50240; Basic Red 2); 1,4-dim ethyl-5-[(4-(dimethylamino)phenyl)azo]-1,2,4-triazolium-chloride (C.I. 11055; Basic Red 22);

2-[((4-Dimethylamino)phenyl)azo]-1,3-dimethyl-1H-imidazolium chloride (Basic Red 51); 2-hydroxy-1-[(2-methoxyphenyl)azo]-7-(trim ethylammonio)-naphthalin-chloride (C.I. 12245; Basic Red 76); bis[4-(dimethylamino)phenyl][4-(methylamino)phenyl] carbenium chloride (C.I. 42535; Basic Violet 1); 4-[(4-amino-m-tolyl)(4-imino-3-methylcyclohexa-2,5-dien-1-ylidene)methyl]-o-toluidine monohydro chloride (Basic Violet 2); tris[4-(dimethylamino)phenyl]carbenium chloride (C.I. 42555; Basic Violet 3); [9-(2-carboxyphenyl)-6-(diethylamino)xanthen-3-ylidene]-diethylazanium chloride (C.I. 45170; Basic Violet 10); di(4-aminophenyl)(4-amino-3-methylphenyl)carbenium-chloride (C.I. 42510; Basic Violet 14); 3H-Indolium, 2-[2-[4-(diethylamino)phenyl]ethenyl]-1,3,3-trim ethyl-chloride (Basic Violet 16); 9-(dimethylamino)-benzo[a]phenoxazin-7-ium-chloride (C.I. 51175; Basic Blue 6); Phenoxazin-5-ium, 3-(diethylamino)-7-(phenylamino)-, trichlorozincate (1-) (Basic Blue 75) di[4-(diethylamino)phenyl][4-(ethylamino)naphthyl]carbenium-chloride (C.I. 42595; Basic Blue 7); 3,7-di(dimethylamino)phenothiazin-5-ium-chloride (C.I. 52015; Basic Blue 9); 1-methyl-amino-4-(amino-N-propyltrimethylammonium)anthraquinone methylsulfate (C.I. 61512; Basic Blue 22); di[4-(dimethylamino)phenyl][4-(phenylamino)naphthyl]carbenium-chloride (C.I. 44045; Basic Blue 26); 2-[(4-(ethyl(2-hydroxyethyl)amino)phenyl)azo]-6-methoxy-3-methyl-benzothiazolium-methylsulfate (C.I. 11154; Basic Blue 41); 4-[(2,6-dichlorophenyl)(4-imino-3,5-dimethyl-2,5-cyclohexadien-1-ylidene) methyl]-2,6-dim ethylaniline phosphate (1:1) (C.I. Basic Blue 77); 3-[(4-amino-6-bromo-5,8-dihydro-1-hydroxy-8-imino-5-oxo-2-naphthalenyl)amino]-N,N,N-trimethylbenzenaminium chloride (C.I. 56059; Basic Blue 99); 3-Amino-7-(dimethylamino)-2-methoxyphenoxazin-5-ium chloride (Basic Blue 124); bis[4-(diethylamino)phenyl]phenylcarbenium-hydrogen sulfate(1:1) (C.I. 42040; Basic Green 1); 1,3-bis [(2,4-diamino-5-methylphenyl)azo]-3-m ethylbenzene (C.I. 21010; Basic Brown 4); 1-[(4-aminophenyl)azo]-7-(trimethyl ammonio)-2-naphthol-chloride (C.I. 12250; Basic Brown 16); 1-[(4-amino-2-nitrophenyl) azo]-7-(trimethylammonio)-2-naphthol-chloride (C.I. 12251; Basic Brown 17), N,N-dimethyl-3-{[4-(methylamino)-9,10-dioxo-9,10-dihydro-1-anthracenyl] amino}-N-propyl-1-propanaminium bromide (HC Blue No. 16); and also 2-((4-(acetylamino)phenyl) azo)-4-methylphenol (C.I. 11855; Disperse Yellow 3); 1-(4'-aminophenylazo)-4-nitrobenzene (C.I. 11005; Disperse Orange 3); 1-[di(2-hydroxyethyl)amino]-3-methyl-4-[(4-nitrophenyl)azo]-benzene (C.I. 11210, Disperse Red 17) and 4-((4-(di(2-hydroxyethyl)amino) phenyl)azo)-aniline (Disperse Black 9); 9,10-Anthracenedione, 1-[(2-hydroxyethyl)amino]-4-[(3-hydroxypropyl)amino]- (Disperse blue 377).

Other dyes suitable are HC blue 18, HC Red 18, HC Yellow 16.

Examples of azo direct dyes, described in the Colour Index International, 3rd edition, comprise: Acid Yellow 1; Acid Yellow 9; Acid Yellow 23; Acid Yellow 36; Acid Orange 7; Acid Orange 24; Acid Red 33; Acid Red 35; Acid Red 92; Acid Violet 43; Acid Violet 49; Acid Blue 1; Acid Blue 3; Acid Blue 9; Acid Blue 62; Acid Black 1; acid yellow 3, acid green 25, acid blue 7.

These dye compounds may be contained in the composition of the invention in amounts from about 0.01 to 4.0 percent by weight.

Examples of natural direct dyes according to the invention include lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used and, especially, henna-based poultices or extracts.

The total amount of dyes can range from 0.01 to 10 percent, preferably from 0.01 to 8% by weight of the composition.

Suitable alkalizing agents may be selected from ammonium carbonate, ammonium hydrogen carbonate, sodium carbonate, sodium hydrogen carbonate as well as ammonium hydroxide, monoethanolamine (MEA), 1-amino-2-propanol, 2-amino-2-methyl-propanol (AMP), 2-amino-2-methyl-1,3-propanediol, 2-amino-2-ethyl-1,3-propanediol, tris(hydroxymethyl)-aminomethane (tromethamine, Tris), potassium Hydroxide, sodium hydroxide and tetrahydroxypropyl ethylenediamine (Neutrol TE).

The compositions may also contain a combination of at least one inorganic alkaline reacting salt with at least one alkanolamine.

The total amount of alkaline reacting agent can vary from 0.5 to 10 percent by weight of the composition.

Auxiliary agents may be for instance ammonium chloride, ammonium citrate, triammonium phosphate or amino acids, such as glycine or arginine, and salts thereof.

Suitable hydrogen peroxide compositions are preferably in form of cream, liquid or gel which can be stabilized as usually. The concentration of hydrogen peroxide may vary in a wide range, commercially available aqueous solutions of 3%, 6%, 9%, or 12% strength being preferred.

Preferably, the solutions having the above standard strengths are mixed with the dye solutions in a 1:1, 1:1.5 or 1:2 ratio, whereby the hydrogen peroxide concentration in the ready-to-use composition normally does not exceed 8%, preferably 6% by weight of the composition, ore preferably ranging from 1 to 6% by weight of the composition. The amount of the hydrogen peroxide adduct ranges from 2.5% to 17% by weight of the composition.

Besides hydrogen peroxide, it is also possible to use a hydrogen peroxide adduct from which hydrogen peroxide is split off, for example a urea-hydrogen peroxide adduct (urea peroxide, carbamide peroxide), a melamine-hydrogen peroxide adduct (melamine peroxide), an amino acid-hydrogen peroxide adduct typified by a histidine-hydrogen peroxide adduct (histidine peroxide). Preferably, urea peroxide is used.

The amount of released hydrogen peroxide normally does not exceed 8% by weight referred to the ready-to-use composition, preferably it does not exceed 6%. More preferably, the hydrogen peroxide adduct provides an on-head concentration of 1 to 6% by weight of the composition.

The compositions may also comprise tensides selected from anionic, neutral, amphoteric or cationic surface-active compounds.

Anionic tensides are selected from the group consisting of alkylsulfate, alkylethersulfate, alkylsulfonate, alkylarylsulfonate, alkylsuccinate, alkylsulfosuccinate, N-alkoylsarcosinate, acyltaurate, acylisethionate, alkylphosphate, alkyletherphosphate, alkylethercarboxylate, alpha-olefinsulfonate, and salts thereof, such as sodium, ammonium and triethanolamine salts.

The alkylethersulfate, alkyletherphosphate and alkylethercarboxylate may comprise between 1 to 10 ethylenoxide or propylenoxide units, preferably 1 to 3 ethylenoxide-units per molecule.

Preferred tensides are sodium laurylsulfate, ammonium lauryl sulfate, sodium laurylethersulfate, ammonium laurylethersulfate, sodium lauroylsarcosinate, sodiumoleylsuccinate, ammonium laurylsulfosuccinate, sodium dodecylbenzolsulfonate, triethanolamidodecylbenzolsulfonate.

Suitable amphoteric tensides comprise alkylbetaine, alkylamidopropylbetaine, alkylsulfobetaine, alkylglycinate, alkylcarboxyglycinate, alkylamphoacetate or propionate, alkylamphodiacetate or dipropionate, such as for example cocodimethyl sulfopropylbetain, laurylbetaine, cocamidopropylbetaine or sodium cocamphopropionate.

Examples of further suitable cationic tensides include quaternized ammonium compounds such as cetyltrimethylammonium chloride (INCI: cetrimonium chloride), hydroxyethylcetyldimonium phosphate (INCI: Quaternium-44), Luviquat® Mono LS (INCI: cocotrimonium methosulfate), poly(oxy-1,2-ethanediyl), (octadecylnitrilio)tri-2,1-ethanediyl)tris-(hydroxy)-phosphate (INCI Quaternium-52).

The tensides, useful as foaming agents, may be used from 0.1 to 20 percent by weight of the composition, preferably from 1 to 10 percent by weight calculated in form of the pure compounds.

The composition according to the invention may also contain cationic polymers with the INCI name Polyquaternium, such as for example copolymers of vinylpyrrolidone/N-vinylimidazolium salts (products commercially available under the name "Luviquat®"), copolymers of N-vinylpyrrolidone/dimethylaminoethyl methacrylate, quaternized with diethylsulfate, copolymers of N-vinylc aprolactam/N-vinylpyrrolidone/N-vilylimidazolium salts; cationic cellulose derivatives (Polyquaternium-4 and -10), acrylamide/diallyldimethylammonium chloride copolymers (Polyquaternium-7). A particularly preferred cationic polymer is the optionally crosslinked poly(methacryloyloxyethyltrimethylammonium chloride) with the INCI name Polyquaternium-37. The copolymers of acrylic acid and dimethyldiallyl ammonium chloride with the INCI name Polyquaternium-22 and supplied by Lubrizol with name MERQUAT® are particularly preferred.

The preferred on-head amount of such polymers may vary from 0.01 to 1% by weight, more preferably from 0.01 to 0.5% by weight of the composition.

The composition of the invention may also contain one or more additive. The additives may be used in lower amounts, such as stabilizers and complexing agents, and are preferably selected from: salicylic acid, 8-hydroxyquinoline, 1-hydroxyethane-1,1-diphosphonic acid, ethylenediamine tetraacetic acid (EDTA), ethylenediamine-N,N'-disuccinic acid (EDDS), iminodisuccinic acid and the corresponding sodium or ammonium salts.

A perfume and special active like proteins, amino acids, vitamins and sugars may also be optionally added.

Auxiliary agents may be used in variable amounts from 1 to 10% by weight of the composition, whereas the additives may be used in much lower amounts, e.g. in amounts from 0.1 to 1.0% by weight each of the composition.

The pH of the ready-to-use composition may be between 7.5 and 11.5, preferably from 8.5 to 10.5.

The composition of the invention is a solution having a viscosity ranging from 10000 to 250000, preferably from 15000 to 180000 cP at 22° C.

The ready-to-use compositions free of any insoluble materials are ideal for being applied to the dry hair by brush and bowl or a shaker device.

The processing time is predominantly depending from the design of the colorants and the target shades and is usually between 10 minutes up to 1 hour. Shorter processing times are chosen for fast developing colorants which normally require a somewhat higher dye load compared to colorants which require a standard processing time of 30 minutes.

The application temperatures for the dyeing method according to the invention may be in a range between 15 and 45° C. After the contact time, the hair dye is removed from the hair by rinsing, optionally with the help of a shampoo. There is no need to wash the hair with a shampoo if a strong surfactant-containing carrier was used.

The invention solves the prior art problems providing drip-free, stable hair colorant compositions without viscosity fluctuation during shelf life and having improved manageability during application with bowl and brush, good tackiness to the hair, brightness and evenness from growth to tips. All these factors ensure easy and fast application combined with outstanding performance.

EXAMPLES

Unless otherwise indicated, all values in the following tables are in weight percent.

Example 1: Hydrogen Peroxide

The recipes of the developer compositions given in Table 1 represent widely used standard compositions (not inventive). The pH of the compositions is 3.0.

TABLE 1

| Ingredients | Formulation | |
|---|---|---|
| | Example A | Example B |
| Fatty alcohol | up to 5.00 | up to 5.00 |
| Fatty alcohol ethoxylates | up to 3.00 | up to 3.00 |
| Hydrogen peroxide 35% | 17.14 | 25.71 |
| Disodium pyrophosphate | 0.05 | 0.05 |
| Sodium stannate | 0.10 | 0.10 |
| Etidronic acid | 0.04 | 0.04 |
| Pentasodium pentetate | 0.07 | 0.07 |
| Phosphoric acid 85% | 0.16 | 0.16 |
| Water | ad 100 | ad 100 |
| Developer concentration | 6% by weight | 9% by weight |
| Developer Volume | 20V | 30V |

Example 2: Gel

The compositions reported in the table 2 represent two standard base (composition C and D) in comparison with inventive base (Composition E).

TABLE 2

| INGREDIENTS (INCI) | Composition C | Composition D | Composition E* |
|---|---|---|---|
| AQUA | Ad 100 | Ad 100 | Ad 100 |
| PROPYLENE GLYCOL | 7 | 7 | 7 |
| HYDROXYETHYLCELLULOSE | 2 | 2 | 2 |
| SODIUM POLYACRYLATE | 1.5 | — | — |
| CARBOMER | — | 1 | 1 |
| ACRYLATES/METHACRYLAMIDE COPOLYMER | — | — | 0.3 |

TABLE 2-continued

| INGREDIENTS (INCI) | Composition C | Composition D | Composition E* |
|---|---|---|---|
| ETHANOLAMINE | 1.66 | 1.66 | 1.66 |
| AMMONIA | 1.5 | 1.5 | 1.5 |
| PARFUM (FRAGRANCE) | 0.6 | 0.6 | 0.6 |
| SODIUM SULFITE | 0.5 | 0.5 | 0.5 |
| ERYTHORBIC ACID | 0.3 | 0.3 | 0.3 |
| EDTA | 0.2 | 0.2 | 0.2 |
| TOLUENE-2,5-DIAMINE SULFATE | 2.14 | 2.14 | 2.14 |
| 4-CHLORORESORCINOL | 1.367 | 1.367 | 1.367 |
| P-AMINOPHENOL | 0.736 | 0.736 | 0.736 |
| M-AMINOPHENOL | 0.701 | 0.701 | 0.701 |
| 2,4-DIAMINOPHENOXYETHANOL HCl | 0.074 | 0.074 | 0.074 |
| 2-AMINO-3-HYDROXYPYRIDINE | 0.031 | 0.031 | 0.031 |

*Inventive composition

Table 3 reports the parameters and values observed during course test on a inclined plane of 1.5 g of respective mixture of composition C, D and E with mix ratio of 1:1 with composition A. The three mixtures were left slide down the inclined plane for 30 minutes and after that time Speed (ratio between distance covered and time of 30 minutes), Length (distance covered in 30 minutes) and Elongation (difference between up and down frontage of mixture at the end minus the same at the beginning) were measured and calculated. The Composition E, according to the invention, obtained the minor speed, length and elongation.

TABLE 3

| TESTED PARAMETER | Composition C | Composition D | Composition E* |
|---|---|---|---|
| Speed (cm/min) | 0.27 | 0.07 | 0.03 |
| Length (cm) | 8 | 2 | 0.9 |
| Elogantion (cm) | 6.42 | 1.67 | 0.4 |

Table 4 shows the data of the difference in viscosity before and after 3 months at 40° C. for composition D and E or relative mixture 1:1 with Activator B. The rheological property fluctuation after stability is less for composition E as well as its mixture.

TABLE 4

| TESTED PARAMETER | Composition D | Composition E* |
|---|---|---|
| Composition Viscosity fluctuation after 3 months at 40° C. (cP) | 8000 | 2700 |
| Mixture Viscosity fluctuation after 3 months at 40° C. (cP) | 5000 | 3000 |

The composition D and E have also been tested on a model by a hairdresser using bowl and brush.

Hairdresser gave a score from 1 to 3 (1: bad, 2 good and 3: very good) for parameters reported in table 5 during application.

TABLE 5

| PARAMETERS | Composition D | Composition E* |
|---|---|---|
| PREVENTED DRIP FROM BRUSH | 1 | 3 |
| TACKINESS TO THE HAIR | 1 | 3 |
| EVENESS | 2 | 3 |
| BRIGHTNESS | 2 | 3 |

Composition E mixed with activator of Formula A in 1:1 ratio showed the best results in term of prevent drip from brush, tackiness to the hair, evenness and brightness.

Example n. 3. Compositions of the Invention

| INGREDIENTS (INCI) | Comp. F | Comp. G | Comp. H | Comp. I | Comp. L | Comp. M | Comp. N | Comp. O | Comp. P | Comp. Q |
|---|---|---|---|---|---|---|---|---|---|---|
| AQUA (WATER) | Ad 100 | Ad 100 | Ad 100 | Ad 100 | Ad 100 | Ad 100 | Ad 100 | Ad 100 | Ad 100 | Ad 100 |
| PROPYLENE GLYCOL | 7 | 7 | 7 | 7 | 7 | 7 | 7 | 7 | 7 | 7 |
| HYDROXYETHYLCELLULOSE | 2 | 2 | 2 | 2 | 2 | 2 | 2 | 2 | 2 | 2 |
| SODIUM POLYACRYLATE | — | — | — | 2.5 | 1.5 | — | — | — | — | — |
| CARBOMER | 1 | 1 | 1 | 0.5 | 0.5 | 1 | 1 | 1 | 1 | 1 |
| ACRYLATES/METHACRYLAMIDE COPOLYMER | 0.1 | 0.5 | 1 | 0.3 | 0.3 | 0.3 | 0.3 | 0.3 | 0.3 | 0.3 |
| ETHANOLAMINE | 1.66 | 1.66 | 1.66 | 1.66 | 1.66 | 1.66 | 5 | 3 | 1.66 | 1.66 |
| ARGININE | — | — | — | — | — | — | — | — | 8 | — |
| POTASSIUM HYDROXIDE | — | — | — | — | — | — | — | 1 | 0.5 | 2 |
| AMMONIA | 1.5 | 1.5 | 1.5 | 1.5 | 1.5 | 3 | — | — | — | — |
| SOJA PROTEIN | 0.2 | 0.2 | 0.2 | 0.2 | 0.2 | 0.2 | 0.2 | 0.2 | 0.2 | 0.2 |
| ALLANTOIN | 0.1 | 0.1 | 0.1 | 0.1 | 0.1 | 0.1 | 0.1 | 0.1 | 0.1 | 0.1 |
| 4-T-BUTYLCYCLOHEXANOL | 0.2 | 0.2 | 0.2 | 0.2 | 0.2 | 1 | 1 | 1 | 1 | 1 |
| MENTHOL | 0.2 | 0.2 | 0.2 | 0.2 | 0.2 | 0.2 | 0.2 | 0.2 | 0.2 | 0.2 |
| PARFUM (FRAGRANCE) | 0.6 | 0.6 | 0.6 | 0.6 | 0.6 | 0.6 | 0.6 | 0.6 | 0.6 | 0.6 |
| SODIUM SULFITE or METABISULFITE | 0.5 | 0.5 | 0.5 | 0.5 | 0.5 | 0.5 | 0.5 | 0.5 | 0.5 | 0.5 |
| ERYTHORBIC ACID | 0.3 | 0.3 | 0.3 | 0.3 | 0.3 | 0.3 | 0.3 | 0.3 | 0.3 | 0.3 |
| EDTA | 0.2 | 0.2 | 0.2 | 0.2 | 0.2 | 0.2 | 0.2 | 0.2 | 0.2 | 0.2 |
| TOLUENE-2,5-DIAMINE SULFATE | 0.978 | 0.978 | 0.978 | 0.978 | 0.978 | — | — | — | — | — |
| P-PHENYLENDIAMINE | 0.2 | 0.2 | 0.2 | 0.2 | 0.2 | — | — | — | — | — |
| 4-CHLORORESORCINOL | 0.01 | 0.01 | 0.01 | 0.01 | 0.01 | — | — | — | — | — |
| N,N-BIS(2-HYDROXYETHYL)-P-PHENYLENEDIAMINE SULFATE | 0.01 | 0.01 | 0.01 | 0.01 | 0.01 | 1.511 | 1.511 | 1.511 | 1.511 | 1.511 |
| HYDROXYETHYL-P-PHENYLENEDIAMINE SULFATE | — | — | — | — | — | 1 | 1 | 1 | 1 | 1 |
| RESORCINOL | 0.01 | 0.01 | 0.01 | 0.01 | 0.01 | — | — | — | — | — |
| 2-METHYL RESORCINOL | 0.01 | 0.01 | 0.01 | 0.01 | 0.01 | 0.05 | 0.05 | 0.05 | 0.05 | 0.05 |
| P-AMINOPHENOL | 0.5 | 0.5 | 0.5 | 0.5 | 0.5 | — | — | — | — | — |
| M-AMINOPHENOL | 0.191 | 0.191 | 0.191 | 0.191 | 0.191 | — | — | — | — | — |

-continued

| INGREDIENTS (INCI) | Comp. F | Comp. G | Comp. H | Comp. I | Comp. L | Comp. M | Comp. N | Comp. O | Comp. P | Comp. Q |
|---|---|---|---|---|---|---|---|---|---|---|
| 4-AMINO-M-CRESOL | 0.001 | 0.001 | 0.001 | 0.001 | 0.001 | 0.1 | 0.1 | 0.1 | 0.1 | 0.1 |
| 2,4-DIAMINOPHENOXYETHANOL HCL | 0.3 | 0.3 | 0.3 | 0.3 | 0.3 | 0.2 | 0.2 | 0.2 | 0.2 | 0.2 |
| 5-AMINO-6-CHLORO-O-CRESOL | 0.1 | 0.1 | 0.1 | 0.1 | 0.1 | — | — | — | — | — |
| 2-AMINO-4-HYDROXYETHYLAMINO-ANISOLE SULFATE | 0.271 | 0.271 | 0.271 | 0.271 | 0.271 | 0.2 | 0.2 | 0.2 | 0.2 | 0.2 |
| 1-NAPHTOL | 0.001 | 0.001 | 0.001 | 0.001 | 0.001 | — | — | — | — | — |
| 5-AMINO-4-CHLORO-O-CRESOL | 0.1 | 0.1 | 0.1 | 0.1 | 0.1 | — | — | — | — | — |
| p-METHYLAMINOPHENOL SULFATE | 0.001 | 0.001 | 0.001 | 0.001 | 0.001 | 0.01 | 0.01 | 0.01 | 0.01 | 0.01 |
| 3-AMINO-2,6-DIMETHYLPHENOL | 0.001 | 0.001 | 0.001 | 0.001 | 0.001 | 0.1 | 0.1 | 0.1 | 0.1 | 0.1 |
| 2-AMINO-3-HYDROXYPYRIDINE | 0.4 | 0.4 | 0.4 | 0.4 | 0.4 | 0.1 | 0.1 | 0.1 | 0.1 | 0.1 |
| 2-METHYL-5-HYDROXYETHYLAMINOPHENOL | 0.2 | 0.2 | 0.2 | 0.2 | 0.2 | 0.335 | 0.335 | 0.335 | 0.335 | 0.335 |
| 1-HYDROXYETHYL 4,5-DIAMINO PYRAZOLE SULFATE | 0.01 | 0.01 | 0.01 | 0.01 | 0.01 | 0.01 | 0.01 | 0.01 | 0.01 | 0.01 |
| 4-AMINO-2-HYDROXYTOLUENE | 0.1 | 0.1 | 0.1 | 0.1 | 0.1 | 0.415 | 0.415 | 0.415 | 0.415 | 0.415 |
| HC Blue n° 7 | — | — | — | — | — | 0.097 | 0.097 | 0.097 | 0.097 | 0.097 |
| HC BLUE 2 | 0.1 | 0.1 | 0.1 | 0.1 | 0.1 | 0.1 | 0.1 | 0.1 | 0.1 | 0.1 |
| 2-AMINO-6-CHLORO-4-NITROPHENOL | 0.1 | 0.1 | 0.1 | 0.1 | 0.1 | 0.05 | 0.05 | 0.05 | 0.05 | 0.05 |

The invention claimed is:

1. Ready-to-use gel compositions for coloring hair in the form of an aqueous solution comprising:
   at least one Acrylates/Methacrylamide Copolymer;
   at least one cellulose derivative;
   at least one cross-linked polymer of acrylic acid or methacrylic acid or salts thereof;
   at least one oxidation dye and optionally at least one direct dye;
   at least one alkalizing agent;
   hydrogen peroxide or a hydrogen peroxide adduct.

2. Ready-to-use gel compositions according to claim 1 wherein the cellulose derivatives are selected from acetyl, methyl or ethyl celluloses, hydroxyalkyl celluloses or carboxyalkyl celluloses.

3. Ready-to-use gel compositions according to claim 2 wherein the cellulose derivative is hydroxyethylcellulose.

4. Ready-to-use gel compositions according to claim 1 wherein the acrylates/Methacrylamide Copolymer is present an amount from 0.01 to 10 percent by weight of the composition.

5. Ready-to-use gel compositions according to claim 1 wherein hydroxyethylcellulose is present an amount from 0.01 to 4.0% by weight of the composition.

6. Ready-to-use gel compositions according to claim 1, further comprising direct dyes.

7. Ready-to-use gel compositions according to claim 6 wherein the direct dyes are selected from neutral, acidic or cationic nitrobenzene direct dyes; neutral, acidic or cationic azo direct dyes; neutral, acidic or cationic quinones, azine direct dyes, triarylmethane direct dyes, indoamine direct dyes and natural direct dyes.

8. Ready-to-use gel compositions according to claim 1, wherein the alkalinizing agent is selected from ammonium carbonate, ammonium hydrogen carbonate, sodium carbonate, sodium hydrogen carbonate as well as ammonium hydroxide, monoethanolamine, 1-amino-2-propanol, 2-amino-2-methyl-propanol, 2-amino-2-methyl-1,3-propanediol, 2-amino-2-ethyl-1,3-propanediol, tris(hydroxymethyl)-aminomethane, potassium hydroxide, sodium hydroxide and tetrahydroxypropyl ethylenediamine.

9. Ready-to-use gel compositions according to claim 1, wherein hydrogen peroxide is in form of cream, liquid or gel or in form of aqueous solutions of 3%, 6%, 9%, or 12% strength.

10. Ready-to-use gel compositions according to claim 1 wherein hydrogen peroxide is in form of an urea-hydrogen peroxide, a melamine-hydrogen peroxide adduct, an amino acid-hydrogen peroxide adduct.

11. Ready-to-use gel compositions according to claim 1 further comprising tensides selected from anionic, neutral, amphoteric or cationic surface-active compounds.

* * * * *